(12) United States Patent
Parra

(10) Patent No.: US 6,265,835 B1
(45) Date of Patent: *Jul. 24, 2001

(54) ENERGY-EFFICIENT ULTRAVIOLET SOURCE AND METHOD

(76) Inventor: Jorge M. Parra, 10721 Skyhawk Dr., New Port Richey, FL (US) 34654

( * ) Notice: Subject to any disclaimer, the term of this patent is extended or adjusted under 35 U.S.C. 154(b) by 0 days.

This patent is subject to a terminal disclaimer.

(21) Appl. No.: 09/456,988

(22) Filed: Dec. 7, 1999

Related U.S. Application Data

(63) Continuation-in-part of application No. 09/168,850, filed on Oct. 9, 1998.

(51) Int. Cl.$^7$ ................................................. H05B 41/16
(52) U.S. Cl. ..................... 315/246; 315/209 R; 315/291; 315/46; 210/748; 210/243
(58) Field of Search ..................... 315/291, 219, 315/129, 246, 267, 307, 209 R; 210/748, 243, 175

(56) References Cited

U.S. PATENT DOCUMENTS

| | | |
|---|---|---|
| 4,172,981 | 10/1979 | Smith ........................................ 307/66 |
| 4,482,809 | 11/1984 | Maarschalkerweerd ............. 250/436 |
| 4,872,980 | 10/1989 | Maarschalkerweerd ............. 250/243 |
| 5,023,518 | 6/1991 | Mans et al. ............................ 315/219 |
| 5,081,399 | 1/1992 | Jy ............................................. 315/121 |
| 5,230,792 | 7/1993 | Sauska et al. .......................... 210/97 |
| 5,324,423 | 6/1994 | Markham ................................. 210/87 |
| 5,401,394 | 3/1995 | Markham ................................. 210/85 |
| 5,495,143 | * 2/1996 | Lengyel et al. ....................... 313/574 |
| 5,503,800 | 4/1996 | Free ........................................ 422/24 |
| 5,536,395 | 7/1996 | Kuennen et al. ....................... 210/87 |
| 5,547,590 | 8/1996 | Szabo .................................... 210/748 |
| 5,611,918 | 3/1997 | Markham ................................. 210/87 |
| 5,698,091 | 12/1997 | Kuennen et al. ....................... 210/87 |
| 5,707,594 | 1/1998 | Austin ................................. 422/186.3 |
| 5,866,984 | 2/1999 | Doughty et al. ..................... 313/643 |
| 6,037,722 | * 3/2000 | Moisin .................................. 315/307 |

* cited by examiner

Primary Examiner—Don Wong
Assistant Examiner—Tuyet T. Vo
(74) Attorney, Agent, or Firm—Jim Zegeer

(57) ABSTRACT

A ballast-free energy-efficient ultra-violet material treatment and purification system and method having an ultraviolet (UV) source comprising a gas discharge UV lamp having spaced electrodes, a source of a high-frequency (about 100 kHz to about 1.5 MHz) alternating-current square-wave voltage and connected directly to the spaced electrodes to non-thermionically start and operate the gas discharge UV lamp. Proportionate control of the intensity of UV generation is provided. A plurality of UV lamps are serially connected and started and operated by a high-frequency alternating-current square-wave voltage.

19 Claims, 2 Drawing Sheets

ENERGY-EFFICIENT ULTRAVIOLET SOURCE AND METHOD

REFERENCE TO RELATED APPLICATIONS

This application is a continuation-in-part of my copending application Ser. No. 09/168,850 filed Oct. 9, 1998 and entitled LOW-VOLTAGE BALLAST-FREE ENERGY-EFFICIENT ULTRAVIOLET MATERIAL TREATMENT AND PURIFICATION SYSTEM AND METHOD.

This application is also related to U.S. application Ser. No. 08/942,670 filed Oct. 2, 1997 entitled LOW-VOLTAGE NON-THERMIONIC BALLAST-FREE FLUORESCENT LIGHT SYSTEM AND METHOD which in turn was the subject of provisional application Ser. No. 60/053,796 filed Jul. 25, 1997 which are incorporated hereby reference. This application is also a continuation-in-part of my application Ser. No. 08/964,824 for LOW VOLTAGE NON-THERMIONIC BALLAST-FREE ENERGY-EFFICIENT LIGHT-PRODUCING GAS DISCHARGE SYSTEM AND METHOD filed Nov. 5, 1997 and incorporated herein by reference.

Reference is also made to my application Ser. No. 08/915,696 filed Aug. 21, 1997 entitled LOW-VOLTAGE HIGH-EFFICIENCY FLUORESCENT SIGNAGE, PARTICULARLY EXIT SIGN and incorporated herein by reference.

BACKGROUND AND BRIEF DESCRIPTION OF THE INVENTION

In a typical fluid treatment purification system utilizing ultraviolet (UV) energy, the fluid, which may be a liquid and/or gaseous substance contaminated by pathogenic organisms is moved through a treatment zone. Typically, the UV energy is provided by causing a discharge in a gaseous medium contained in a UV transmissive bulb or envelope. Typical gas fillings include mixtures of argon (and/or other gases such as xenon XE, krypton KR) and mercury which, upon discharge therein, is rich in ultraviolet (other UV rich gases on ionization may be used). Typically, a ballast power supply is connected to the electrodes. In electronic ballast systems, a step-up transformer provides a high striking or ionization voltage, several hundred volts (which, once the lamps are energized, is lowered to a normal operating voltage (normally in the range of 100–200 volts)).

When the ultraviolet lamps are used for large scale water purification and treatment systems, the lamps, typically a cylindrical ultraviolet ray-emitting lamp and an outer coaxial and substantially coextensive cylindrical UV transparent sleeve, are arranged in banks or arrays in parallel rows. Various structural arrangements are utilized to enable and facilitate the mounting of the banks or arrays of UV lamps in a water-flow conduit for treatment of the water. Typically, the axis of the UV lamps are parallel to the flow direction of the water.

In some systems, the UV source is driven in two or more intensity modes, a low intensity mode when the fluid flow is low and a high intensity mode when the fluid flow is high. Reference is made to the following prior U.S. patents:

| U.S. Pat. No. | Issued  | Inventors        |
| ------------- | ------- | ---------------- |
| 4,482,809     | 11/1984 | Maarschalkerweerd |
| 4,872,980     | 10/1989 | Maarschalkerweerd |
| 5,023,518     | 06/1991 | Mans et al       |
| 5,081,399     | 01/1992 | Jy               |
| 5,230,792     | 07/1993 | Sauska et al     |
| 5,324,423     | 06/1994 | Markham          |
| 5,401,395     | 03/1995 | Markham          |
| 5,503,800     | 04/1996 | Free             |
| 5,536,395     | 07/1996 | Kuennen et al    |
| 5,547,590     | 08/1996 | Szabo            |
| 5,611,918     | 03/1997 | Markham          |
| 5,698,091     | 12/1997 | Kuennen et al    |
| 5,707,594     | 01/1998 | Austin           |

Sauska et al U.S. Pat. No. 5,230,792 and Markham U.S. Pat. No. 5,611,918 are typical examples of ultraviolet water purification systems with variable intensity controls. In these patents, the intensity of an ultraviolet lamp is controlled by a circuit which is responsive to fluid flow for selectively energizing the lamp to provide variable UV intensity output depending upon fluid flow. In these circuits, a high striking voltage is required to initiate the discharge and produce ultraviolet. In the case of Sauska et al, the circuit arrangement is such that the ultraviolet lamp is always started with a high-current ballast. This is in order to assure the striking of a discharge, and then a low-mode ballast is used to maintain the UV lamp in the low output stage status.

THE PRESENT INVENTION

The object of the present invention is to provide an improved ultraviolet energy source and, more particularly to provide a ballast-free energy-efficient ultraviolet energy source, and still more particularly to provide such a UV source in a fluid treatment system and yet more particularly to provide a significantly more efficient, low-current, ultraviolet light-producing system for treatment of various fluids and substances and materials and water treatment useful in killing and/or controlling pathogens, microorganisms, bacterial and other deleterious materials in flowing fluid systems such as water purification and air purification systems.

The UV energy produced by the invention can be used for curing, UV medical treatments and diagnostics, tanning salons, photolithographic applications, signalling systems, imaging systems enhancing chemical reactions, detection systems, destruction of undesired vegetation, optical recording systems, insect attractants, in situ dental, etc.

Since the ultraviolet energy source of the present invention is significantly lower in power consumption and produces significantly more useful ultraviolet energy/per watt than conventional ultraviolet energy lamps and bulbs that it replaces, fewer lamp units for a given treatment may be required; and since there is no heated filament, the lamps have longer lifetimes. In addition, since the intensity level can be varied from zero to high intensity and back to zero in an infinitely variable manner, the intensity rate of the ultraviolet energy can be varied in a likewise infinitely variable manner (e.g. step-less variations).

Since heated filaments are not utilized, the device is essentially non-thermionic.

According to the invention, one or more ultraviolet lamps are started and operated from an alternating-current square-wave power supply driver circuit. The square-wave power supply driver circuit incorporates a solid state switch circuit which is operated to generate a substantially square-wave alternating-current voltage at the ultraviolet lamp or tube electrodes, such that the square-wave alternating-current voltage applied to the electrodes reverses polarity more rapidly than the pattern of electron and ion density in the UV tube can shift so that electrons throughout the length of the space between the electrodes are continually accelerated and will, through several cycles of the applied square-wave voltage, create free electrons and ions throughout the tube volume and ionize the gas-producing ultraviolet energy in a discharge. In the preferred embodiment, the oscillating frequency is set in the range from about 100 kHz to about 1.5 MHz and, more precisely, between 1 MHz and 1.5 MHz. In preferred embodiments, there are no high voltages in the driver circuit so safer operation is assured. Variation in intensity levels can be achieved by varying the voltage or energy level from the direct current supply to the driver circuit. In a preferred embodiment, care is taken to assure that there are no spike voltages due to inductive kicks and the like. Since the ultraviolet lamps or devices are non-thermionically driven, e.g. the filaments are not heated, the efficiency of UV production is significantly improved. Moreover, at the high-frequency range, the power supply can be much smaller.

Another feature of the present invention is that in comparison to traditional ultraviolet lamp systems there is marked reduction in current, power consumption and heat, accompanied by significant increase in ultraviolet light energy output which, in turn, is the reason why efficient conversion of electricity to ultraviolet energy is high. Some of the heat (power) reduction is, of course, recognizable as resulting from the absence of direct heating of the filaments in each end of the tube by applied voltages. Some is also explained in terms of energy transfer in the high-field region which occurs near the momentary cathode. However, ultraviolet lamps in the system of the present invention are much cooler throughout their length including areas that are the greatest distances from the filaments or electrodes whose heating could not possibly be explained by conduction, radiation or diffusion heat transferred through the low pressure gas filling the tube. The alternating-current square-wave AC at about 75 kHz to about 1.5 MHz with the preferred range being about 1.0 MHz to about 1.5 MHz depending in part on the atomic particles (of a given gas discharge medium).

Cooling along the length of the tube is believed to be explainable in terms of energy transferred to electrons and ions by the applied electric field. In the present invention, the square-wave applied voltage to the tube reverses so frequently that positive ions in the discharge can build up little kinetic energy during a half-cycle of the applied voltage. In conventional ultraviolet lighting systems driven by discharge (e.g. non-microwave or magnetron driven UV system), larger amounts of energy can be acquired by ions in one-half cycle. This kinetic energy contributes nothing to ultraviolet light production, but in conventional systems is rapidly transferred to neutral gas molecules and thence to the walls of the tube.

A major source of energy loss in conventional ultraviolet tubes is caused by the need to almost completely reconstitute ionization in the tube at the beginning of each half-cycle. This requires not only energy to ionize electrically neutral gas molecules, but additional energy representing losses when electrons collide with neutral gas molecules and thereby increase their motional energy without ionizing the molecules. The fact that the system is non-thermionic and ballast-free (the same square-wave voltage waveform is used to start and operate the UV lamp) eliminates the danger and cause of electrical fires caused by overheated ballast-driven systems.

DESCRIPTION OF THE DRAWINGS

The above and other objects, advantages and features of the invention will become more apparent when considered with the following specification and accompanying drawings wherein.

DETAILED DESCRIPTION OF THE INVENTION

The present invention is based on the discovery, disclosed in my above identified applications, that using a rapidly repetitive high-frequency square-wave alternating voltage, ionization will take place in gas discharge devices in the absence of a "striking" voltage at significantly lower voltages and power. Since the half-cycle period of the square-wave alternating voltage power according to the invention is very short (of the order of 0.5 microseconds for 1 MHz or 5 microseconds for 100 kHz), there is very little opportunity for decay of the plasma between half-cycles. At start-up, ambient free electrons in the gas increase in energy in a half-cycle more than they lose energy due to collision processes. According to the invention, during one half-cycle, an electron will move in a roughly constant electric field. During each interval between collisions with neutral atoms, or ions, its kinetic energy will increase if its previous collision left it traveling with a component of velocity in the direction of the acceleration produced by the electric field. It will decrease if its previous collision left it moving without a component of velocity opposed to the field's acceleration. According to the invention, the square-wave alternating supply voltage serves principally to raise the effective electron energy (or temperature). The current flowing consists of electrons flowing to the instantaneous anode and positive ions flowing to the instantaneous cathode where they recombine with electrons and are released as neutral atoms. Total gas pressure in the tube is sufficient to make the mean free path considerably less than the tube diameter and much less than its length. Most electrons and ions separate and recombine, in a small fraction of the overall length of the tube, rather than flowing as continuous streams along its axis.

If free electrons and ions fill the space between the UV lamp electrodes, the electrons are pulled toward the anode, and the positive ions toward the cathode, until in the space between there is no longer a field and therefore no means to cause further movement of the particles; a voltage drop, that is, region of high field, will exist very close to each of the two electrodes. The electrons (and ions) in the main part of the tube will not be further affected by the field; when electrons reach the high field region near the anode, they will probably be accelerated to half the applied voltage within less than one mean free path of the anode's surface and hence will be unlikely to produce ionization.

Figure 1:
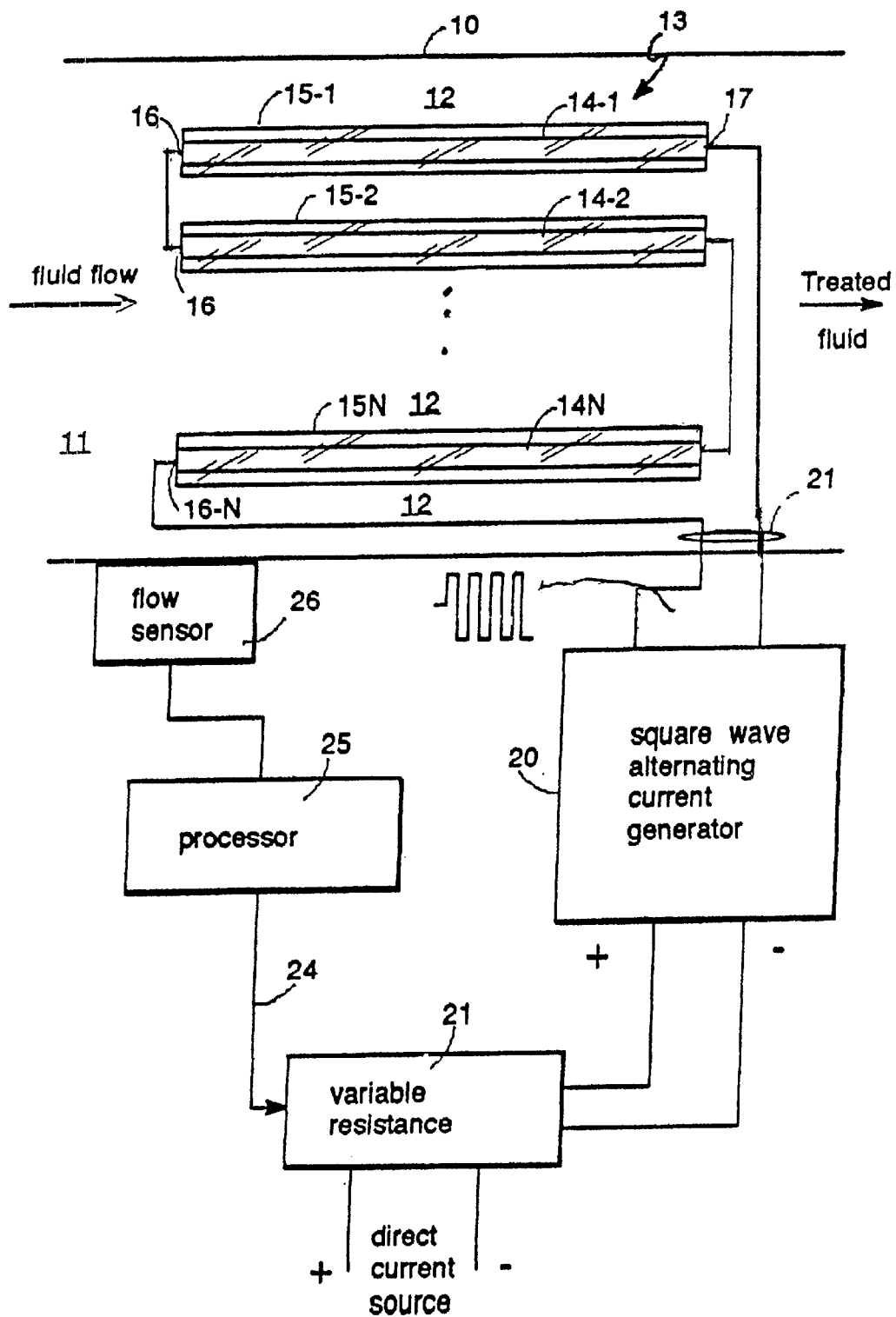
FIG. 1 is a general block diagram of a fluid flow ultraviolet purification and treating system incorporating the invention.
Figure 2:
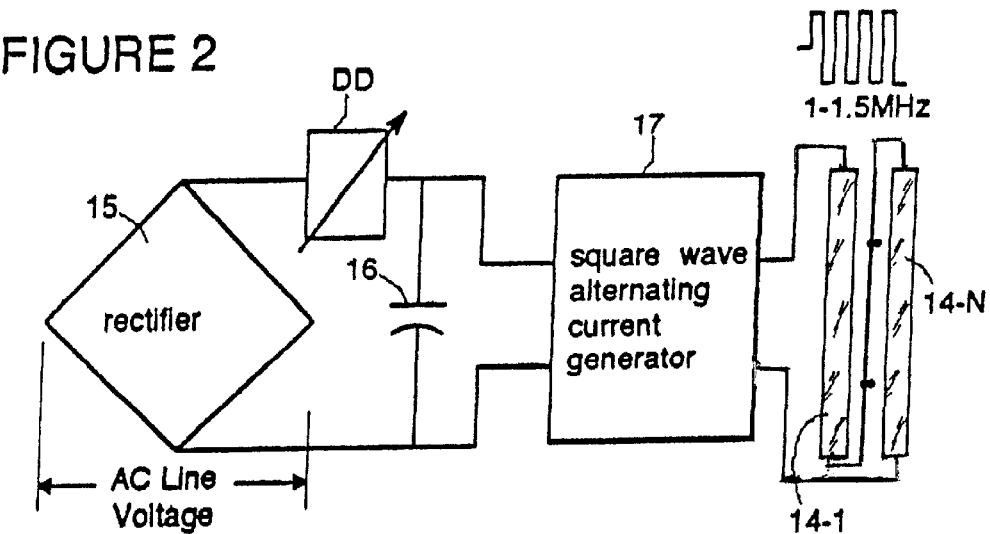
FIG. 2 is a general block diagram of a square-wave alternating-current generator incorporating the invention.

Referring now to FIG. 1, a passage or conduit 10 contains a flowing fluid 11 which, in this present case, is water. A treatment zone 12 is provided with an array 13 of ultraviolet lamps or tubes 14-1, 14-2 . . . 14-N which are contained within usually transparent quartz tubes 15-1, 15-2. UV tubes or bulbs 14-1, 14-2 . . . 14-N are connected in electrical series and are filled with a conventional gas discharge mixture which is rich in UV production upon discharge, such as 90% argon, 10% neon and 3%–5% of mercury at a pressure of about 10 millibars or Thors. Instead of heated filaments, each tube may contain electrodes 16, 17, of the type usually found in neon signage. Of course conventional UV tubes, with the filaments (unheated) serving as non-thermionic electrodes, can be used. The electrodes 16, 17 are connected to a square-wave alternating-current generator 20 by lead wires 21. The lead wires 21 need not be expensive or heavily insulated. Square-wave alternating-current generator 20 is supplied with direct current from a direct current source which may be a bridge rectifier 15 (FIG. 2) connected to an alternating-current supply. In a preferred embodiment of the present invention, a variable resistance 21 is interposed between the direct current voltage supply and the square-wave alternating generator 20 so that the intensity level of ultraviolet energy can be varied by varying the direct current supply to the square-wave alternating-current generator. The adjustment of the intensity level of ultraviolet light production from low (or zero)-to-high and high-to-low is thus simply and easily achieved.

Referring to FIG. 1, in still a further preferred embodiment of the invention, a flow sensor 22 detects the rate of flow of fluid in conduit or passage 10 and the rate of flow signal output of flow sensor 22 is fed to microprocessor 23 which outputs an intensity control signal 24 which is used to control variable resistance 21. Thus, on no flow of fluid 11 in passage or conduit 10, the flow sensor output is zero so that the processing control signal output is zero so that the variable resistance 21 is essentially high or an open circuit. As fluid flow begins, the flow sensor signal increases and the processor 23 output control signal 24 causes variable resistance 21 to decrease thereby supplying more energy to square-wave alternating-current generator 20, thereby increasing the energy supplied on lines 21 to the electrodes of serially connected UV lamps 14-1, 14-2 . . . 14-N. Thus, as the rate of waterflow reaches the maximum, the maximum energy is supplied to the UV tubes thereby increasing the amount of the ultraviolet energy used to treat the fluent material flowing in conduit 10 to a maximum. Since the controls are variable from zero to a maximum, the maximum ultraviolet energy coincides with the maximum fluid flow rate and the minimum or zero ultraviolet energy coincides with the zero flow rate, and any place in-between the ultraviolet energy generated is directly proportional to the fluid flow rate.

Moreover, the current rate is very low, so, in comparison with ultraviolet output of conventional ultraviolet purification lamps driven by conventional 60 cycle thermionically (heated filaments) operated fluorescent tubes or lamps, the luminous efficiency is significantly improved. Moreover, the ultraviolet lamps or tubes can be straight, folded, helical, looped, etc. Reflectors and UV lenses can be used with the lamps.

Rheostat or variable resistance 21R is used to adjust or vary the voltage or energy level from the direct current source to the ultraviolet lamp device and thereby dim or vary the intensity of ultraviolet rays produced by the lamps. It will be appreciated that while the UV lamps are shown driven from a single square-wave alternating-current generator a plurality of square-wave alternating-current generators can be provided, one for each lamp (or set of serially connected lamps) and each individually controlled according to individual flow conditions adjacent a given lamp or sector. In other words, there can be a plurality of flow sensors, one for each UV lamp or cluster or array of UV lamps controlling the UV production in their energy levels at each lamp in infinitesimally small increments of adjustment. Thus, since the system does not depend on a large or striking ignition voltage level, the energy level from the ultraviolet lamp can be varied from very low to high and back to low. In contrast, the prior art requires a high striking voltage to initiate a discharge in the ultraviolet lamps and cannot start out at low levels as is the case of the present invention.

Figure 3:
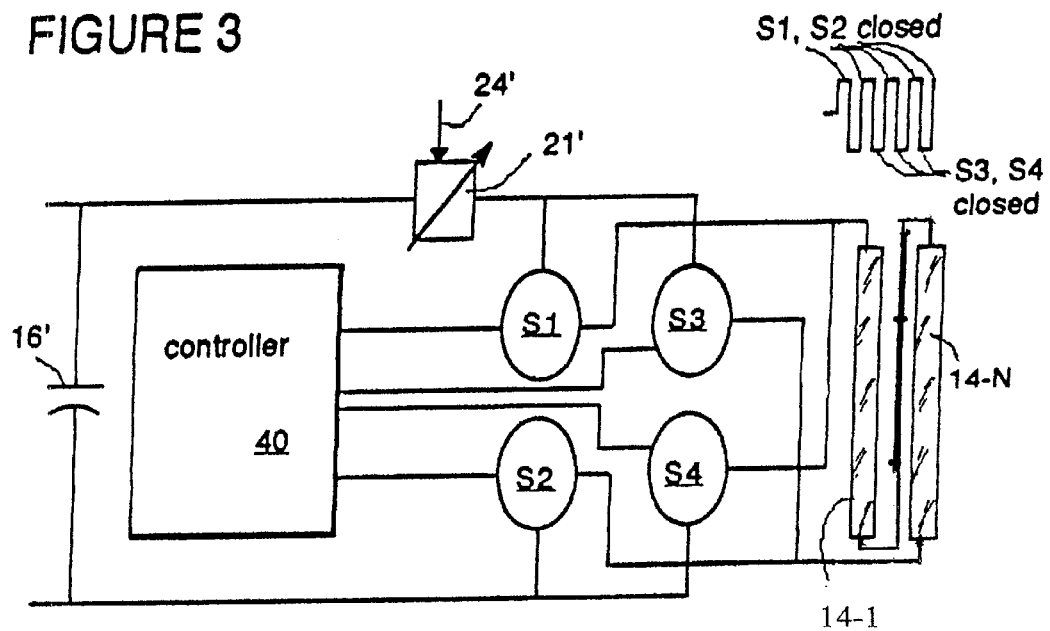
FIG. 3 is a generalized circuit diagram of a square-wave alternating-current generator incorporating the invention.

In FIG. 3, a transformerless square-wave invertor circuit is illustrated wherein the positive (+) and negative (−) terminals of a direct current source are alternately connected to opposing electrodes of the ultraviolet lamp(s). In this case, when switches SI and S2 are closed simultaneously or at the same time, preferably by the same signal from controller 40, the positive terminal (+) is connected to electrode E-1 and the negative terminal (−) is connected directly to electrode E-2. When the switches S3 and S4 are simultaneously closed (and switches S1 and S2 are open) by controller 40, the positive terminal (+) is connected directly to lamp electrode E-2 and the negative terminal (−) is connected to the electrode E-1 of the ultraviolet lamp. Controller 40 can operate the switches in the range of about 75 kHz to about 1.5 MHz and preferably operates the switches to cause the square-wave voltage applied to lamp electrodes E-1 and E-2 to be at a frequency of about 1 MHz to about 1.5 MHz.

In this invention, the magnitude of the alternating voltage at the electrodes is of small significance in initiating the discharge reaction, allowing the capability to start the production of ultraviolet light at a low or high intensity—since the generated ultraviolet is in direct proportion to the total energy input.

While preferred embodiments of the invention have been described and illustrated, it will be appreciated that other embodiments, adaptations and modifications of the invention will be readily apparent to those skilled in the art.

What is claimed is:

1. In a fluid purification system in which fluid flowing in a path is subjected to ultraviolet (UV) energy, the improvement comprising:

a fluid flow rate sensor for measuring the fluid flow rate of fluid flowing in said path and producing a fluid flow rate control signal, an ultraviolet (UV) source positioned in said path, said UV source having a UV lamp and a square-wave alternating-current driver current connected to said UV lamp to non-thermionically start and operate said lamp with a square-wave alternating-current voltage having a frequency in the range of 75 kHz to about 1.5 MHz, a controller connected to said ultraviolet source and said flow rate sensor for proportionately controlling the intensity of ultraviolet energy emitted in said path by said intensity control as a function of said control signal.

2. A plurality of serially connected ultraviolet lamps and a high-frequency, square alternating-current square-wave voltage directly connected to said serially connected ultraviolet lamps to non-thermionically start and operate all said ultraviolet lamps, said high frequency being between about 75 kHz and 1.5 MHz.

3. A non-thermionic driver circuit for starting and operating an ultraviolet lamp comprising a square-wave alternating current voltage source having a frequency from between about 75 kHz to about 1.5 MHz and means for connecting said square-wave alternating current voltage source directly to said ultraviolet lamp device to start and operate the same.

4. In an ultraviolet (UV) treatment system, the improvement comprising an ultraviolet (UV) source, said UV source comprising in combination:

at least one UV lamp and a source of high-frequency, square-wave alternating voltage in the frequency range of about 75 kHz to about 1.5 MHz connected to non-thermionically start and operate said UV lamp.

5. The ultraviolet material treatment system defined in claim 4 including a device for proportionally varying the UV intensity level from said UV lamp.

6. A non-thermionic method of starting and operating an ultraviolet (UV) lamp device having spaced electrodes immersed in a gas at voltages far below the required starter ignition voltage for cold cathodes comprising:

providing a square-wave alternating voltage source having a frequency of between about 75 kHz and 1.5 MHz, and applying said square-wave alternating voltage from said source directly to said UV device so that the voltage on said UV lamp device electrodes reverses its polarity more rapidly than the pattern of electron and ion density in the gas can shift.

7. The method defined in claim 6 including varying the energy level from said source to said UV lamp to vary the UV energy level emitted thereby.

8. An ultraviolet (UV) source comprising at least a pair of serially connected UV lamps and a source of high-frequency square-wave alternating voltage directly connected to non-thermionically start and operate said at least a pair of serially connected UV lamps.

9. The UV source defined in claim 8 wherein said source of high-frequency square-wave alternating voltage is variable to vary the intensity of UV generated by said lamps.

10. A fluid purification system comprising a fluid flow path, a treatment zone in said fluid flow path and one or more of the UV source defined in claim 8 in said treatment zone.

11. The UV source defined in claim 10 wherein said source of high-frequency square-wave alternating voltage is variable.

12. The invention defined in claim 10 including a flow rate sensor for measuring fluid flow rate in said treatment zone and producing a control signal for said variable source to vary the UV intensity level of said UV source.

13. An ultraviolet (UV) source comprising in combination a gas discharge UV lamp having spaced electrodes, a source of a high-frequency alternating-current square-wave voltage and a circuit directly applying said high-frequency alternating current square-wave voltage to said spaced electrodes to non-thermionically start and operate said gas discharge UV lamp.

14. The UV source defined in claim 13 wherein said high-frequency square-wave voltage is in the frequency range of about 75 kHz to about 1.5 MHz.

15. The UV source defined in claim 14 wherein said high-frequency square-wave voltage has a frequency of about 1 MHz.

16. The UV source defined in claim 13 wherein there are a plurality of said gas discharge UV lamps connected electrically in series.

17. The UV source defined in claim 16 wherein said voltage has a frequency in the range of about 75 kHz to about 1.5 MHz.

18. The UV source defined in claim 13 including a device for controlling the energy level of said source of square-wave alternating-current voltage supplied to said UV lamp.

19. The UV source defined in claim 18 wherein said device for controlling includes a rheostat.

* * * * *